United States Patent [19]

Posorske

[11] 4,371,552
[45] Feb. 1, 1983

[54] PRUNE JUICE PRODUCTION USING CELLULASE

[75] Inventor: Laurence H. Posorske, Bethel, Conn.

[73] Assignee: Novo Industri A/S, Denmark

[21] Appl. No.: 300,322

[22] Filed: Sep. 8, 1981

Related U.S. Application Data

[63] Continuation of Ser. No. 121,146, Feb. 13, 1980, abandoned.

[51] Int. Cl.³ .......................... A23L 1/28; A23L 2/04
[52] U.S. Cl. ....................................... 426/50; 426/51; 426/52; 426/599
[58] Field of Search ................... 426/51, 52, 50, 599

[56] References Cited

U.S. PATENT DOCUMENTS

| | | | |
|---|---|---|---|
| 3,346,392 | 10/1967 | Lowe et al. | 426/481 |
| 3,615,721 | 10/1971 | Silberman | 426/52 |
| 3,795,521 | 3/1974 | Richard | 426/51 |

FOREIGN PATENT DOCUMENTS 2038544  2/1972  Fed. Rep. of Germany ........ 426/49

OTHER PUBLICATIONS

Woodroof, J. G. & Phillips, G. F.; *Beverages: Carbonated and Noncarbonated;* AVI Publishing Co., 1974; pp. 59 & 60.
Rombouts et al., *Process Biochemistry,* vol. 13, No. 8, Aug. 1978, pp. 9-13.

*Primary Examiner*—Raymond N. Jones
*Assistant Examiner*—Elizabeth J. Curtin
*Attorney, Agent, or Firm*—Fidelman, Wolffe & Waldron

[57] ABSTRACT

The disintegration process for prune juice production is improved through cooking prunes until substantial disintegration has taken place followed by treatment with cellulase, e.g., the cellulase of *Trichoderma reesei*, and optionally with a pectinase, which allows for good yield recovery of prune juice through centrifugal separation.

8 Claims, No Drawings

PRUNE JUICE PRODUCTION USING CELLULASE

This is a continuation of application Ser. No. 121,146, filed Feb. 13, 1980 now abandoned.

BACKGROUND OF THE INVENTION

Prune juice is currently produced by one of two methods. The "diffusion" method involves leaching the soluble solids from dried prunes by successive 2-4 hour hot water extractions for a total time of about 12 hours. The combined extracts are then concentrated to 18.5% solids or greater to produce the finished juice. In the "disintegration" method, the prunes are disintegrated by 2-3 hours of cooking in boiling water. The juice, containing 18.5% soluble solids or greater, is then separated from the disintegrated pulp and the pits by pressing and/or filtration.

The diffusion process is time-consuming and gives relatively low yields of clear juice with a moderate viscosity. The disintegration process is much faster and gives higher yields of juice with a relatively high viscosity, but is much more energy intensive.

In the early 1970's a modification of the disintegration process focused on the use of pectinase enzymes was proposed. Pectinase treatment of the partially disintegrated prunes shortens the cooking time and results in energy savings. The enzyme treatment also improves filterability of the disintegrated prunes. However, pectinase treated juice has a very low viscosity. Because high viscosity is important to the organoleptic quality of prune juice, the modified process (which produces a low viscosity juice) has not met with great success in commerce.

Another modification to the current practice of the disintegration process that was proposed (along with the enzyme treatment step) is separation of the juice from the prune pulp residue by centrifugation rather than filtration. The centrifugal separation procedure is appealing since it does not require addition of a filter aid and the residue does not contain significant levels of the filter aid. Unfortunately, good yields cannot be obtained by centrifugation of prunes disintegrated in the normal fashion. Centrifugal separation is only feasible for recovering the low viscosity juice from prune mixtures that have been treated with pectinase, and, therefore, this too has not been adopted in commercial practice.

RATIONALE OF THE INVENTION

It is believed that the differences in results obtained by the varying processes of diffusion, disintegration, and enzymatic treatment, can be understood by appreciating that each treatment has its own unique affect on the complex structure and materials of the cell walls inside the prune.

The diffusion procedure leaves many cell wall membranes intact, requiring then that the hot water leach solubles cross such membranes. High molecular weight soluble substances would tend to be retained behind an intact membrane. Likely, high molecular weight color bodies present behind intact membranes (from hydrolysis reactions and/or carmelizing reactions) might not be leached into the prune juice. The relatively low yield, moderate viscosity, and relatively clear juice which characterise the diffusion process prune juice are results consistent with presence of intact cell wall membranes in the prune residue.

The disintegration procedure fractures many, and perhaps all, cell membranes, releasing thereby soluble high molecular weight materials. The improved yield, higher viscosity, greater color (vis a vis the diffusion process) characteristic of disintegration process prune juice are results consistent with complete rupture of cell wall membranes.

Pectinase (when included in the disintegration process) enzymatically attacks the pectin content of the cell walls. Adding an enzymatic attack on cell walls to the affects of mechanical action and of cooking should have process consequences, such as reduced cooking time. However, pectinase also attacks dissolved pectin. Degradation of soluble high molecular weight materials in the juice, is then the consequence to which the reduced viscosity characteristic of pectinase treated prune juice products.

Since reduction in viscosity has been considered a detriment by the prune juice art, it would appear that process improvements in the prune juice art should be tailored toward creating a prune juice that satisfies all the properties heretofore characteristic of commercially available prune juices, including, for example, solids content of greater than 18.5° Brix, viscosity of 7 to 15 cps and, of course, acceptable taste characteristics.

Elaborating further on the present hypothesis that rupture of cell wall membranes is a major key to improved prune juice yield, and hopefully to creating a prune residue of improved processing characteristics, it should be noted that pectin is not the only ingredient of cell walls and that the cell wall membranes might well be ruptured by attack on a component other than pectin. Specifically, attacking the cellulose content of the cell wall with a cellulase should rupture the cell wall. Desirably, the cellulase employed for this purpose should have little or no pectinolytic activity, so that the viscosity reduction in prune juice attributable to enzymatic degradation of dissolved pectins will not take place. A particularly suitable cellulase is the cellulase of *Trichoderma reesei*; this cellulase is virtually free of pectinase activity.

Preferred practice of this invention involves treatment of prunes with the cellulase of *Trichoderma reesei*.

OBJECTS OF THE INVENTION

The principal object of this invention is to provide an improved process for obtaining high quality prune juice.

A further object of this invention is to provide a prune juicing process of improved thermal economy.

Still another object of this invention is to provide a disintegration method for juicing prunes that allows for centrifugal separation of prune juice from prune pulp, which results in prune residue with lower ash content.

SUMMARY OF THE INVENTION

This invention comprises a process for producing prune juice of moderate to high viscosity by treating a partially disintegrated mixture of prunes in water with a cellulase, and optionally with pectinase, at 40° C. to 60° C. for 30 minutes to six hours, preferably at about 50° C. for 2-4 hours. The prune juice then can be separated from the prune pulp either by centrifugation or by filtration according to practices heretofore suggested to the art. The prune juice produced according to practice of this invention will have good viscosity, be produced in adequate yield and will leave a prune residue separable by centrifugating; all the results being comparable to the best obtained by prune juicing practice heretofore.

DISCUSSION OF THE INVENTION

In practice of this invention the mixture of prunes and water are treated initially as has been done heretofore. Specifically the prunes ground or whole, with or without the pits are cooked with water e.g., 1-4 pounds of water per pound of prunes, at about 100° C. Neither the cooking method nor cooking time is critical, but since minimum expenditure of thermal energy is desired, cooking for less than about one hour is preferred for practice of this invention. The cooking insures that at least partial disintegration of the prunes have taken place prior to the enzymatic treatment. If the process commences with whole prunes, they are largely disintegrated after about 30 minutes of cooking. Thus, practice of this invention contemplates cooking the dried prunes (pitted or unpitted, whole or ground prunes) for 15-90 minutes.

In any event the whole or preground cooked prunes may be depitted by screening the mixture e.g., through a 7-mesh screen. The pits are, of course, not disintegrated by cooking.

Treatment with the cellulase is carried out for ½-6 hours at 40° C.-60° C., which temperatures are well suited to the *Trichoderma reesei* cellulase. Treatment at more elevated temperatures than 60° C. involve rapid deactivation of this enzyme, while treatment at less than 40° C. heightens the danger of microbial contamination of the prune juice and, needlessly, lengthens treatment time or enzyme usage or both. Treatment with the cellulase at 50° C.-55° C. for 2-4 hours is preferred. Generally, enzymatic treatment time is inverse to treatment temperature e.g., 30 minutes at 60° C., 6 hours at 40° C.

As already has been indicated, the cellulase preferred for practice of this invention is the *Trichoderma reesei* cellulase. This particular cellulase has little or no pectinase activity, so the viscosity of the juice is not degraded by hydrolysis of soluble pectins. Controlled amounts of commercial pectinase enzymes can be added to increase juice yield without the danger of viscosity loss caused by contaminant pectinase activity in the *Trichoderma reesei* cellulase.

Thus, the cellulase attacks the cell wall, rupturing membranes that otherwise might remain intact and interfere with the juicing process. The yield improvement which is characteristic of this process is attributed primarily to a release (from the prune residue) of soluble substances, rather than to any solubilization affect of the enzymatic digestion. The juice is recovered without a material decrease in viscosity. Thus, cellulase enhanced disintegration is comparable to the usual non-enzyme enhanced disintegration process.

As in virtually all enzyme catalyzed reactions, the cellulase is employed in low dosages, using 0.01-0.75% preferably 0.05-0.25% by wt. based on the weight of the depitted prunes slurry of a *Trichoderma reesei* cellulase, having 1000 units/gm of enzyme. In activity terms, practice of this invention contemplates from 100 to 7500 cellulase units per kg of depitted prunes, 500 to 2500 units being a preferred range. (One cellulase unit produces 1 umole of reducing sugar end groups from 0.4% carboxymethyl cellulose when incubated at pH=5 and 50° C.) An exemplary treatment of prunes is with 0.1% of commercially available cellulase (Celluclast TM) by wt. for 2 hours at 50° C. following a 30 minutes cook of the prunes in boiling water. As will be detailed hereinafter small proportions of pectinase, e.g., 0.0005% of a commercial pectinase (Pectinex 3X) may be included advantageously.

As compared to conduct of the disintegration method without enzymes, employment of cellulase improves juice yield. However, if the processor is willing to tradeoff some or all of the potential yield improvement for processing advantages, use of cellulase allows the processor to separate the prune juice from the residual prune pulp by centrifugation. In short, the heretofore conventional recovery step of separating prune juice from solids through filtration with the aid of a mineral filter aid may be avoided by use of cellulase during juicing.

The use of cellulase according to practice of this invention does not alter the viscosity characteristic of the prune juice relative to non-enzyme treated prune juice thereby allowing treatment with cellulase to be combined with a pectinase treatment—one mild enough to hold the viscosity drop to tolerable limits, i.e., using from 10 to 200 units of pectinase per kg of depitted prune slurry. (One pectinase unit reduces the viscosity of 40 ml of 1% citrus pectin by 25% in 10 minutes when incubated at pH=3.5 and 30° C.) Inclusion of pectinase within the process increases juice yield still further, apparently through enzymatic solubilization of insoluble ingredients. It is believed that pectin associated with cell wall membranes is solubilized by the pectinase.

The test work indicates that the greatest yield of prune juice per kg of prunes can be obtained by treatment with pectinase alone. Unfortunately, the pectinase treatment is accompanied by an unacceptably high reduction in the viscosity of the prune juice product. However, limiting the pectinase dosage to less than 100 units per kg of depitted prune slurry as is herein contemplated secures the advantage of a significant yield improvement with little lowering in the viscosity of the prune juice product.

Treatment with enzyme, either the cellulase alone or with cellulase and pectinase can be carried out without adjusting pH of the prune juice from its normal level of pH 3.6-3.9. Activity of both enzymes are adequate to the intended purposes at those pH levels.

Allusion has repeatedly been made to recovery of the juice by centrifugation such being preferred according to practice of this invention. For the details of a centrifugation process applicable to separating prune juice from the disintegrated prune residue reference is made to U.S. Pat. No. 3,346,392.

The foregoing discussion of this invention has been entirely in terms of disintegrating the prunes by cooking them in boiling water as if it were the only way to prepare the mixture to be treated enzymatically according to practice of this invention. Such description has been posed for simplicity alone. Other prune cooking procedures are known to the art, including notably the steam screw press method. Any cooking technique may be employed to achieve substantial disintegration, whereafter the cooked mixture is subjected to the enzyme treatment herein described.

For further understanding of practice of this invention, reference is now made to the following examples.

EXAMPLE 1

400 g of whole dried prunes in 800 g water were cooked at 100° C. with vigorous agitation and the distilled vapor returned to the cooking mixture. After 30 minutes the prunes had disintegrated, and the mixture was passed through a 7-mesh screen to remove pits. One hundred gram aliquots of the depitted mixture were treated as described below to recover prune juice.

Centrifugal separation was accomplished at 1200 xg for 10 minutes. The supernate was removed, and the pellet was washed by centrifugation using an amount of water equal to the weight of the supernate. The initial separation gave juice with a dissolved solids concentration of 18.6% by weight or greater, measured by refractometric techniques. Subsequent washing yielded juice of lower solids content which would require evaporation to give 18.6% solids juice. The total yield is based on the sum of 18.6% solids juice from the initial separation plus the amount of 18.6% solids juice potentially available in the wash juice.

Separation by filtration was accomplished by adding Celite ® filter aid equal to 10% by weight of the prune slurry and filtering through paper under vacuum. The filter cake was resuspended in a volume of water equal to one half the original weight of the mixture and refiltered. Yield was computed for the filtration method on the same basis as that used for centrifugal separations.

A commercial cellulase, Celluclast TM, was added to the deposited prune mixture at a dosage of 0.1% by weight. The mixture was held at 50° C. with intermittent agitation for four hours and the juice was then separated by centrifugation.

TABLE I

| ENZYME TREATMENT | SEPARATION METHOD | Yield (gal./ton prunes) | |
|---|---|---|---|
| | | INITIAL SEPARATION | TOTAL |
| None | Centrifugation | 279 | 446 |
| None | Filtration | 382 | 583 |
| 0.1% Celluclast | Centrifugation | 404 | 544 |

Table I shows the yields obtained using the two separation methods along with the yield of juice from prunes treated by cellulase. Yields from the centrifugal process are lower than yields from the filtration process. However, when the prune mixture was treated with cellulase, the initial juice yield and the total yields obtained from centrifugation were close to that obtained by filtration.

TABLE II

| EFFECT OF ENZYME TREATMENT ON JUICE SEPARATED BY A CENTRIFUGAL PROCESS | | | | | | | |
|---|---|---|---|---|---|---|---|
| Enzyme Treatment | | Initial Separation | | | Total | Weight of Waste[c] | |
| Pectinex 3X | Celluclast 100L | Viscosity[a] | pH | Yield[b] | Yield[b] | Wet | Dry |
| None | None | 62 | 3.8 | 217 | 433 | 3130 | 581 |
| 0.0005% | .05% | 24 | 3.8 | 339 | 546 | 2480 | 367 |
| 0.005% | .2% | 22 | 3.8 | 348 | 549 | 2422 | 330 |
| .002% | .05% | 16 | 3.8 | 346 | 552 | 2333 | 364 |
| .002% | .2% | 8 | 3.8 | 400 | 569 | 2127 | 330 |
| .01% | .05% | 4 | 3.8 | 401 | 535 | 2174 | 405 |
| .01% | .2% | 4 | 3.8 | 423 | 573 | 1938 | 300 |
| .05% | None | 4 | 3.6 | 453 | 629 | 1798 | 224 |

[a]Viscosity in centipoise
[b]Gallons/ton of prunes
[c]Pounds/ton prunes

EXAMPLE 2

A cooked and depitted prune mixture was prepared as described in Example 1. Aliquots of the mixture were incubated at 50° C. for 2 hours with addition of the enzymes as indicated in Table II. The juice was separated from the pulp by centrifugation as described in Example 1. The weight of washed waste pulp was measured before and after drying for 16 hours at 60° C.

Table II shows that enzyme treatment can increase yield between 50 and 100% in the initial juice separation and 25-50% in the total yield. The greatest yields are obtained with a high concentration of pectinase alone, but this treatment causes a decrease in viscosity detrimental to the quality of the juice. By decreasing the pectinase dosage sharply and including cellulase in the enzyme treatment step, it is possible to obtain sizeable yield enhancements while maintaining an acceptable viscosity level in the prune juice. Table II also shows that increasing pectinase levels lead to lower amounts of wet waste for disposal. Cellulase treatment lowers the amount of dry solids remaining in that waste.

EXAMPLE 3

A cooked and depitted prune mixture was prepared as described in Example 1. Aliquots of the mixture were incubated at 50° C. for 2 hours with the addition of the enzymes indicated in Table III. The juice was separated from the pulp by filtration as described in Example 1. The weight of the washed filter cake before and after drying for 16 hours at 60° C. was measured as the waste.

Table III shows that a properly chosen combination of cellulase and pectinase can give a 30% increase in initial juice yield and a 20% increase in total juice yield without lowering the viscosity of the prune juice below acceptable levels.

Increasing amounts of enzymes cause a decrease in the amount of waste for disposal. The total waste is larger and the effect of enzymes on the waste smaller than in Example 2, since more than half of the solids in the filtration waste are inorganics contributed by the filter aid.

TABLE III

| EFFECT OF ENZYME TREATMENT ON JUICE SEPARATED BY FILTRATION | | | | | | |
|---|---|---|---|---|---|---|
| Enzyme Treatment | | Initial Separation | | Total | Weight of Waste[c] | |
| Pectinex 3X | Celluclast 100L | Viscosity[a] | Yield[b] | Yield[b] | Wet | Dry |
| None | None | 36 | 364 | 526 | 3519 | 880 |
| .0005% | .2% | 30 | 389 | 559 | 2929 | 820 |
| .002% | .05% | 14.4 | 373 | 558 | 3099 | 806 |

TABLE III-continued
EFFECT OF ENZYME TREATMENT ON JUICE SEPARATED BY FILTRATION

| Enzyme Treatment | | Initial Separation | | Total | Weight of Waste[c] | |
|---|---|---|---|---|---|---|
| Pectinex 3X | Celluclast 100L | Viscosity[a] | Yield[b] | Yield[b] | Wet | Dry |
| .002% | .2% | 12.5 | 473 | 610 | 2685 | 725 |
| .02% | None | 4.6 | 473 | 630 | 2586 | 750 |

[a] viscosity in centipoise
[b] gallons/ton of prunes
[c] pounds/ton of prunes

EXAMPLE 4

A mixture of disintegrated prunes was prepared as described in Example 1. Before the depitting step, the mixture was separated into two aliquots. One was passed through a 7-mesh screen for depitting, then treated with 0.05% Celluclast 100 L and 0.01% Pectinex 3X for 2 hours at 50° C. The other aliquot was treated with the enzymes under the same conditions before the depitting step, and passed through the 7-mesh screen afterward. Juice separation by filtration and also by centrifugation was performed as described in Example 1 on 100 g samples of depitted mixture prepared by each method. The results shown in Table IV show that the stage in the process at which enzyme treatment occurs has little effect on the yield or on the residual waste levels obtained.

TABLE IV
ENZYME TREATMENT AT DIFFERENT STAGES IN THE PROCESS

| Enzyme Treatment | Separation Method | Yield[a] | | Waste[b] | |
|---|---|---|---|---|---|
| | | Initial | Total | Wet | Dry |
| Before Depitting Step | Filtration | 592 | 702 | 1781 | 694 |
| After Depitting Step | Filtration | 607 | 668 | 1602 | 609 |
| Before Depitting Step | Centrifugation | 395 | 541 | 1948 | 370 |
| After Depitting Step | Centrifugation | 378 | 492 | 2039 | 387 |

[a] gallons/ton of prunes
[b] pounds/ton of prunes

EXAMPLE 5

A mixture of disintegrated prunes which still contained the pits was prepared as described in Example 1. This mixture was treated for 2 hours at 50° C. with the enzymes indicated in Table V. The juice was then separated from the pit-containing mixture by the centrifugal process described in Example 1. The results are shown in Table V. The yields obtained at various enzyme levels are comparable to the yields seen in previous examples using depitted prune mixtures. The residual waste is higher in this example. This is to be expected since in this example, the waste includes the pits. In the other examples, the pits were removed at an earlier step and were not included in the waste calculations.

TABLE V
PIT REMOVAL BY A CENTRIFUGAL PROCESS

| Enzyme Treatment | Yield[a] | | Waste[b] | |
|---|---|---|---|---|
| | Initial | Total | Wet | Dry |
| None | 263 | 454 | 3981 | 637 |
| .2% Celluclast 100L | 296 | 526 | 3391 | 475 |
| 0.05% Celluclast 100L 0.01% Pectinex 3X | 470 | 648 | 2835 | 369 |
| 0.03% Pectinex 3X | 498 | 673 | 2757 | 303 |

[a] gallons/ton of prunes
[b] pounds/ton of prunes

I claim:

1. A method for obtaining prune juice of viscosity 7–15 cps and exceeding 18.5° Brix which comprises cooking dried prunes until substantial disintegration of the prunes has taken place, then treating the cooked mixture with cellulase for ½–6 hours at a concentration of 100 to 7500 units/kg prune slurry, and with pectinase at a concentration of 10 to 200 units/kg prune slurry and separating the prune juice from the solid prune waste.

2. The method of claim 1 wherein the prune juice and solid prune waste are separated by centrifugation.

3. A method for obtaining prune juice of viscosity 7–15 cps and exceeding 18.5° Brix which comprises cooking dried prunes until substantial disintegration of the prunes has taken place, then treating the cooked mixture with the cellulase of *Trichoderma reesei* at a concentration of 100 to 7500 units/kg prune slurry at 40°–60° C. for 1–6 hours, treatment time being generally inverse to treatment temperature, and thereafter separating the prune juice from solid prune waste.

4. The method of claim 3 wherein the prunes are cooked in boiling water from 15–90 minutes.

5. The method of claim 4 wherein the prune juice and solid prune waste are separated by centrifugation.

6. The method of claim 3 wherein the cooked mixture treated with cellulase is simultaneously treated with pectinase at a concentration of 10 to 200 units/kg of prune slurry.

7. The method of claim 3 wherein treatment with the cellulase is at 50°–55° C. for 2–4 hours.

8. The method of claim 1 wherein the prunes are cooked in boiling water from 15–90 minutes.

* * * * *